(12) United States Patent
Hassan et al.

(10) Patent No.: US 8,317,742 B2
(45) Date of Patent: Nov. 27, 2012

(54) APPLYING SHEAR STRESS FOR DISEASE TREATMENT

(75) Inventors: Abbas Hassan, Sugar Land, TX (US); Rayford G. Anthony, College Station, TX (US); Gregory G. Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 485 days.

(21) Appl. No.: 12/571,580

(22) Filed: Oct. 1, 2009

(65) Prior Publication Data
US 2010/0114061 A1 May 6, 2010

Related U.S. Application Data

(60) Provisional application No. 61/101,867, filed on Oct. 1, 2008.

(51) Int. Cl.
*A61M 37/00* (2006.01)
(52) U.S. Cl. .......................... 604/82; 604/4.01
(58) Field of Classification Search .................. 604/4.01, 604/82–85
See application file for complete search history.

(56) References Cited

U.S. PATENT DOCUMENTS

| | | | |
|---|---|---|---|
| 4,787,883 A * | 11/1988 | Kroyer | ......................... 604/6.13 |
| 4,950,225 A | 8/1990 | Davidner | |
| 5,205,721 A | 4/1993 | Isaacson | |
| 5,538,191 A | 7/1996 | Holl | |
| 5,877,350 A | 3/1999 | Langer et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,530,964 B2 | 3/2003 | Langer et al. | |
| 6,742,774 B2 | 6/2004 | Holl | |
| 2002/0138034 A1 * | 9/2002 | Derek et al. | ................ 604/6.14 |
| 2003/0043690 A1 | 3/2003 | Holl | |
| 2004/0052158 A1 | 3/2004 | Holl | |
| 2005/0033069 A1 | 2/2005 | Holl et al. | |

FOREIGN PATENT DOCUMENTS

WO 02064708 8/2002

OTHER PUBLICATIONS

IKA—The Company, IKA Proudly Manufactures in the USA Catalog, 2011, pp. 1-38.
International Search Report dated Apr. 27, 2010 issued in corresponding international Application No. PCT/US09/59247.

(Continued)

*Primary Examiner* — Kevin C Sirmons
*Assistant Examiner* — Bradley Osinski
(74) *Attorney, Agent, or Firm* — Timothy S. Westby; Porter Hedges LLP (57) ABSTRACT

Herein disclosed is a system for applying shear stress ex-situ to a fluid. In some embodiments, the system comprises a shear device; and at least one device configured for intravenous administration of the fluid to a patient, the devices defining a fluid passage configured to be sterilized and maintained sterile during use, the fluid comprising at least one therapeutic fluid, blood, or a combination thereof. The shear device of the system is in fluid communication with the at least one device configured for intravenous administration of the fluid to a patient. Herein also disclosed is a method of preparing a fluid for intravenous administration to a patient.

11 Claims, 7 Drawing Sheets

OTHER PUBLICATIONS

Hallow, Daniel M. et al. "Shear-Induced Intracellular Loading of Cells with Molecules by Controlled Microfluidics," Biotechnology and Bioengineering, 99(4):846-854 (Mar. 1, 2008).
Brooks, D.E. "The Biorheology of Tumor Cells," Biorheology, 21:85-91 (1984).
Triyoso, Diana H. and Good, Theresa A., "Pulsatile shear stress leads to DNA fragmentation in human SH-SY5Y neuroblastoma cell line," Journal of Physiology, 515.2:355-365 (1999).
Fukuda, Shunichi et al., "Mechanisms for Regulation of Fluid Shear Stress Response in Circulating Leukocytes." Circulation Research 86:313-e18 (2000).
Manzoor, K., "Energy transfer from organic surface adsorbate-polyvinyl pyrrolidone molecules to luminescent centers in ZnS nanocrystals," Solid State Communications 129:469-473 (2004).

* cited by examiner

Figure 1

Therapeutic Fluids

Shear Device

Intravenous Injection/Infusion

Drug Delivery to tumors via passive targeting or to brain across BBB

Figure 4B

APPLYING SHEAR STRESS FOR DISEASE TREATMENT

CROSS-REFERENCE TO RELATED APPLICATIONS

This application claims the benefit under 35 U.S.C. §119(e) of U.S. Provisional Patent Application No. 61/101,867, entitled "Applying Shear Stress For Disease Treatment," filed Oct. 1, 2008, the disclosure of which is hereby incorporated herein by reference in its entirety.

STATEMENT REGARDING FEDERALLY SPONSORED RESEARCH OR DEVELOPMENT

Not Applicable.

FIELD OF THE INVENTION

The present invention generally relates to the treatment of diseases. More particularly, the present invention relates to utilizing a shear device to apply suitable shear stress to therapeutic fluids and/or blood for disease treatment.

BACKGROUND

Because of the complexity of the human body and the complication of various diseases, disease management continues to be the most challenging and active area in medicine. Herein disclosed are a system and an approach to apply shear stress for disease treatment. Some examples of diseases are brain diseases, including meningitis, epilepsy, neurological trypanosomiasis, progressive multifocal leukoencephalopathy. Further examples of diseases are cancers, including malignant neoplasms, benign neoplasms, metastases, and hematological malignancies. Due to the vastness pertaining to this field, brain diseases and cancers are taken as examples to illustrate some important principles and their applications in treating diseases.

Brain diseases remain major clinical challenges despite the fast development in medicine. One of the primary reasons that results in such challenges lies in the structure of the blood-brain barrier (BBB). The blood-brain barrier is composed of high density cells restricting passage of substances from the bloodstream much more than endothelial cells in capillaries elsewhere in the body. It is a membrane in the central nervous system (CNS) that allows the passage of substances essential to metabolic functions (e.g. oxygen) but restricts that of many chemical substances and microscopic objects (e.g. bacteria) between the bloodstream and the neural tissue. This "barrier" derives its function from the selectivity of the tight junctions between endothelial cells in CNS vessels that restricts the passage of solutes. As a result, it is very difficult to deliver drugs to the brain to manage various brain diseases (e.g., meningitis, epilepsy, neurological trypanosomiasis, progressive multifocal leukoencephalopathy); even though suitable drugs are available or will become available. Therefore, it is of vital importance to find methods to deliver drugs to the brain in their nano-size or sub-nano-size forms.

Cancer is one of the greatest threats to human health. According to the 2008 cancer statistics report by the American Cancer Society, cancer caused nearly 560,000 deaths in the United States in 2005, occupying 22.8% of all deaths and ranking as the second killer after heart diseases (26.6% of all deaths). The battle against the threat of cancer continues in clinical, industrial, and research institutions. The understanding of the cause, nature, and progression of various cancer types has led to many methods for cancer treatment, such as surgical excision, chemotherapy, radiotherapy, immunotherapy, and gene therapy.

It is discovered that tumorous tissues exhibit higher activities than normal tissues to recruit blood vessels in order to sustain the over-proliferation of the tumor cells. Furthermore, tumors are not only highly vascularized but also leaky in nature. This has provided the basis for many drug delivery strategies, especially in the case of passive targeting.

Metastases, on the other hand, are the main cause of deaths for cancer patients. Tumor cells shed from primary tumors, enter lymphatic and blood vessels, circulate in the bloodstream, and settle down to grow in other normal tissues in the body. The new tumors are called secondary tumors or metastatic tumors, wherein the cells are like those in the primary tumors. Most primary tumors can metastasize, though in varying degrees (e.g., glioma and basal cell carcinoma rarely metastasize). It is understood that tumorous cells are weaker compared to normal cells. As a result, the change in the environment (e.g., pH, shear stress) can destroy the cancer cells while sparing the healthy/normal cells. Therefore, it is possible to treat the blood (ex-situ) in a shear device so as to destroy the cancer cells that are travelling in the bloodstream while preserving the health of the normal cells, after which the treated blood is re-circulated into the patient via infusion. This method has great value in treating hematological malignancies, such as leukemia, lymphoma, multiple myeloma.

It has also been shown that cellular uptake of molecules is enhanced by exposing them to high shear stress for short durations. This phenomenon renders the potential of loading cells with therapeutic agents as a mechanism for drug delivery and the potential of enhancing drug efficacy while applying shear stress to cancer cells.

SUMMARY

Herein disclosed is a system for applying shear stress ex-situ to a fluid. In some embodiments, the system comprises a shear device; and at least one device configured for intravenous administration of the fluid to a patient, the devices defining a fluid passage configured to be sterilized and maintained sterile during use, the fluid comprising at least one therapeutic fluid, blood, or a combination thereof. The shear device of the system is in fluid communication with the at least one device configured for intravenous administration of the fluid to a patient.

In some embodiments, the system further comprises at least one pump configured to control the flow rate and residence time of a fluid passing through the shear device during use of the system. In some embodiments, the system further comprises at least one pump configured to control the flow rate of the fluid during intravenous administration of the fluid. In some embodiments, the system further comprises at least one temperature control unit configured to control the temperature of the shear device. In some embodiments, the system further comprises at least one temperature control unit configured to control the temperature of a respective device configured for intravenous administration of the fluid to the patient.

In some embodiments, the system further comprises at least one storage vessel in fluid communication with the shear device and the at least one device configured for intravenous administration of the fluid to the patient. In some cases, the system further comprises at least one pump configured to control the flow rate of fluid into or out of the at least one storage vessel. In some embodiments, the system further comprises at least one temperature control unit configured to control the temperature of the at least one storage vessel.

Herein also disclosed is a method of preparing a fluid for intravenous administration to a patient. The method comprises obtaining a system disclosed herein, wherein the fluid passage is sterile; applying shear stress to a fluid selected from the group consisting of therapeutic fluids, blood, and combinations thereof; and maintaining sterility of the fluid and fluid passage.

In some embodiments, the method further comprises controlling temperature of the fluid, wherein shear stress is applied simultaneously with the control of temperature. In some embodiments, the method further comprises controlling the shear stress applied to fluid passing through the shear device. In some embodiments, the method further comprises controlling the residence time of fluid passing through the shear device. In some embodiments, the method further comprises controlling the flow rate of fluid through the shear device.

In some embodiments, the fluid comprises at least one therapeutic agent in the form of a solid, liquid, gas, solution, gel, emulsion, powder or a combination of any of those forms. In some embodiments, the shear stress is applied to therapeutic fluids to disperse the therapeutic agents contained therein to their nano-size or sub-nano-size forms. In some embodiments, the fluid comprises the patients' blood containing both cancer cells and normal blood cells, and applying the shear stress to the fluid destroys mainly cancer cells acutely or chronically without significantly affecting the health or function of the normal cells.

In some embodiments, the fluid comprises a mixture of the patients' blood containing both cancer cells and normal blood cells, and at least one therapeutic agent, and applying the shear stress to the fluid causes at least one of the following effects: (1) destroying mainly cancer cells acutely or chronically without significantly affecting the health or function of the normal cells; (2) dispersing the at least one therapeutic agent to a nano-size or sub-nano-size form; (3) causing intracellular uptake of the at least one therapeutic agent by the cancer cells, resulting in acute or chronic cancer cell death; and (4) causing intracellular uptake of the at least one therapeutic agent by the normal cells without significantly affecting their health or function.

In some embodiments, the fluid comprises at least one therapeutic agent, and applying the shear stress to the fluid activates the at least one therapeutic agent. In some embodiments, activating the at least one therapeutic agent comprises creating free radicals of the at least one therapeutic agent. Here creating free radicals of the therapeutic agents means that the free radicals originate from the therapeutic agents or are associated with the therapeutic agents through various interactions or reactions (physical or chemical).

Furthermore, herein disclosed is a method of performing cell therapy in a patient. The method comprises performing the method described above, wherein the fluid comprises a therapeutic agent and normal blood cells or cancer cells or both, and wherein applying shear stress to the fluid causes intracellular uptake of the at least one therapeutic agent by the normal blood cells or cancer cells or both without significantly affecting the health or function of the normal blood cells; administering the fluid to the patient intravenously to deliver the cells containing the at least one therapeutic agent to a targeted site of agent action in the patient's body through blood circulation; and causing the cells containing the at least one therapeutic agent to release the at least one agent at the targeted site.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

NOTATION AND NOMENCLATURE

As used herein, the term "therapeutic fluids" refers to dispersions that contain at least one substance that has therapeutic effects. Some examples of these substances are neurological drugs, anti-inflammatory drugs, anti-cancer drugs, antibiotics, therapeutic gases (e.g., ozone), viral vectors, genes, proteins, polymers, liposomes, organic particles, inorganic particles.

As used herein, the term "dispersion" refers to a liquefied mixture that contains at least two distinguishable substances (or "phases") that either will or will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is miscible or immiscible, and continuous liquid phases throughout which solid particles are distributed. As used herein, the term "dispersion" encompasses continuous liquid phases throughout which gas bubbles are distributed, continuous liquid phases throughout which solid particles are distributed, continuous phases of a first liquid throughout which droplets of a second liquid that is soluble or insoluble in the continuous phase are distributed, and liquid phases throughout which any one or a combination of solid particles, miscible/immiscible liquid droplets, and gas bubbles are distributed. Hence, a dispersion can exist as a homogeneous mixture in some cases (e.g., liquid/liquid phase), or as a heterogeneous mixture (e.g., gas/ liquid, solid/liquid, or gas/solid/liquid), depending on the nature of the materials selected for combination.

Certain terms are used throughout the following description and claims to refer to particular system components. This document does not intend to distinguish between components that differ in name but not function.

In the following description and in the claims, the terms "including" and "comprising" are used in an open-ended fashion, and thus should be interpreted to mean "including, but not limited to . . . ".

DETAILED DESCRIPTION

Shear Device

Figure 1:
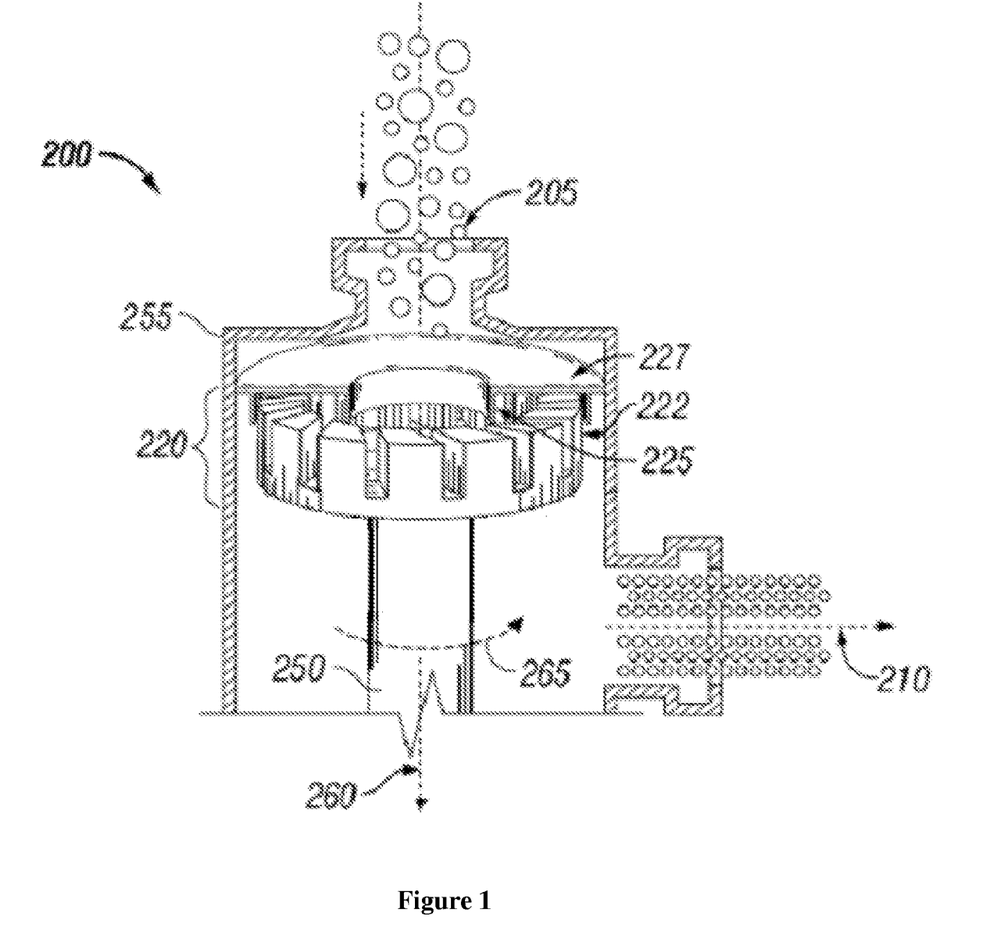
FIG. 1 is a longitudinal cross-section view of a shear device.

FIG. 1 presents a longitudinal cross-section of a suitable shear device 200. Shear device 200 of FIG. 1 is a dispersing device comprising a combination 220 of a rotor 222 and a stator 227. The rotor-stator combination may be known as generator 220 or stage without limitation. The rotor 222 and stator 227 are fitted along drive shaft 250.

For generator 220, the rotor 222 is rotatably driven by input 250 and rotates about axis 260 as indicated by arrow 265. The direction of rotation may be opposite that shown by arrow 265 (e.g., clockwise or counterclockwise about axis of rotation 260). Stator 227 is fixably coupled to the wall 255 of shear device 200. Generator 220 has a shear gap width which is the minimum distance between the rotor and the stator. In the embodiment of FIG. 1, generator 220 comprises a shear gap 225.

Generator 220 may comprise a coarse, medium, fine, and super-fine characterization. Rotors 222 and stators 227 may be toothed designs. Generator 220 may comprise two or more sets of rotor-stator teeth. In embodiments, rotor 222 comprises rotor teeth circumferentially spaced about the circumference of the rotor. In embodiments, stator 227 comprises stator teeth circumferentially spaced about the circumference of the stator.

Shear device 200 is configured for receiving fluid mixtures at inlet 205. Fluid mixtures entering inlet 205 are pumped serially through generator 220, such that product dispersions are formed. Product dispersions exit shear device 200 via outlet 210. Rotor 222 of generator 220 rotates at a speed relative to the fixed stator 227, providing adjustable shear rates. The rotation of the rotor pumps fluid, such as the fluid mixtures entering inlet 205, outwardly through the shear gaps (and, if present, through the spaces between the rotor teeth and the spaces between the stator teeth), creating a localized shear condition. Shear forces exerted on fluid in shear gap 225 (and, when present, in the gaps between the rotor teeth and the stator teeth) through which fluid flows process the fluid and create product dispersion. Product dispersion exits shear device 200 via shear outlet 210.

In certain instances, shear device 200 comprises a ULTRA-TURRAX® of IKA® Works, Inc. Wilmington, N.C. Several models are available having variable sizes, volume capacities, flow rates, tip speeds, inlet/outlet connections, horsepower, output rpm, and operable temperature ranges. For example, the T 10 basic ULTRA-TURRAX® homogenizer provides a stepless control of speed with a speed range of 8000-30000 $min^{-1}$ and adjustable dispersing elements.

In certain embodiments, more than one stage or combination of rotor and stator may be employed. For example, two or three stages of rotor-stator combinations are connected serially along the same drive shaft to enable flexibility to provide variable shear stress. Fluid mixtures are passed through different stages of rotor-stator combinations to be processed serially until the desired dispersion products are formed. Examples of adjustable operational parameters are rotor size, stator size, shear gap, rotor speed, tip speed, shear rate, flow rate, residence time.

Application of Shear Stress

In all embodiments, the entire fluid passage is sterilized and is maintained sterile.

Drug Delivery

In some embodiments, the application of shear stress is especially useful in creating therapeutic dispersions/fluids wherein the therapeutic agents are not miscible or soluble in the continuous phase. For example, ozone as a therapeutic gas is dispersed in phosphate buffer saline (PBS) into gas bubbles that are on the nano or sub-nano scale. When such dispersions are injected or infused into patients, ozone gas is circulated in the bloodstream and transported to various organs and tissues. Because the size of the produced gas bubbles are small (nano-, sub-nano-size), ozone gas has the potential to overcome BBB to obtain access to the brain and therefore become effective therapeutically.

Many other kinds of drugs have low solubility in aqueous solution in the range of room temperature and body temperature. In the same principle as the ozone therapy example, the application of shear stress can create dispersions of such therapeutics, enable their administration to patients, and increase therapeutic efficacy. Some examples are but not limited to anti-inflammatory drugs (e.g., ibuprofen, acetaminophen), anti-cancer drugs (doxorubicin, paclitaxel, 5-fluorouracil), and anti-HIV drugs (e.g., azodicarbonamide). When drugs are dispersed in fluids to nano- and sub-nano-sizes, they can escape being captured by the reticuloendothelial system (RES) and reach the target drug action site via blood circulation.

The fine dispersion of the drug combined with passage through the shear device allows for better absorption of drugs into the cells and tissues, thus making the drugs more effective and reducing adverse effects the drugs have on the liver. This also reduces the amount of drugs required because the liver is not filtering out the drugs. In some cases, the application of shear activates chemotherapy drugs by creating free radicals. These radicals are capable of destroying cancer cells. Thus the application of shear increases the efficacy of the chemotherapy drugs.

Selection of the shear device, shear rate, shear stress, and residence time applied in shear device 200 depends on the amount of therapeutic fluid/dispersion administered and the nature of the components of the therapeutic fluids utilized. The operational parameters are further adjusted according to the objectives of tasks at hand, which dictate the specific requirements for the therapeutic fluids. For example, the dispersion of gases and liquids in a continuous phase may take place at a lower rate and/or for a shorter time than in the case of the dispersion of solids.

Figure 2A:
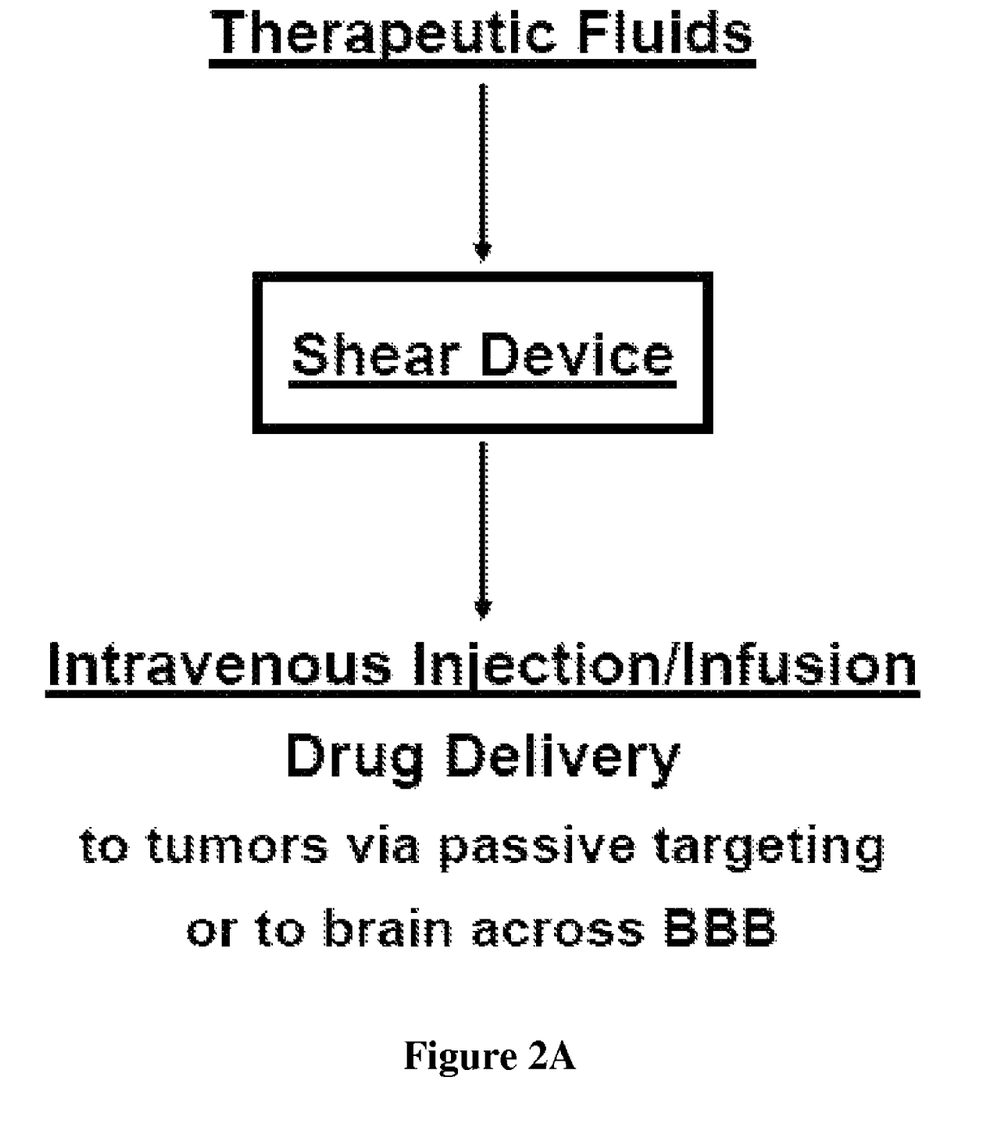
FIG. 2A illustrates a method of utilizing the shear device for drug delivery.

In exemplary embodiments (FIG. 2A), shear stress is applied to therapeutic fluids in drug delivery to treat diseases such as cancers and brain diseases. In alternative embodiments, shear stress is applied in drug delivery to treat diseases according to one's interest and the use of available drugs.

Figure 2B:
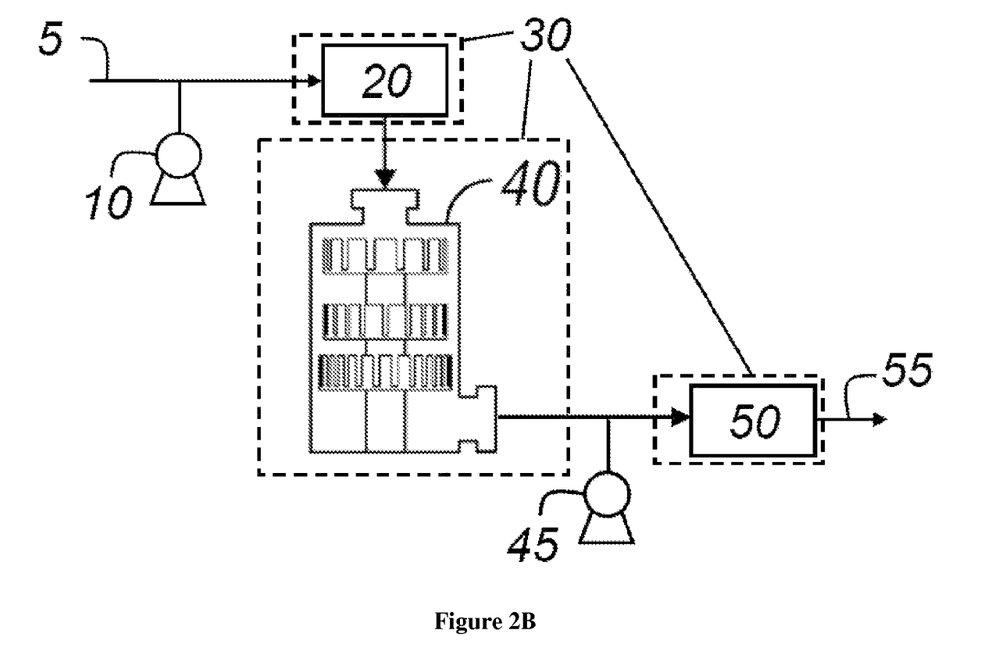
FIG. 2B is a process flow diagram demonstrating the application of shear stress for drug delivery.

In exemplary embodiments (FIG. 2B), therapeutic fluids 5 are transported and stored in a vessel 20 with a temperature control unit 30. Alternatively, the creation of therapeutic fluid 5 is achieved by any other suitable method known to one skilled in the art. The temperature control unit 30 is any device known to one skilled in the art and has the capacity to maintain a temperature between 0-100° C. within ±2° C. fluctuations. In some embodiments, a pump 10 is included to control the flow into vessel 20. Pump 10 is configured for either continuous or semi-continuous operation, and may be any suitable pumping device. Vessel 20 is configured to be in fluid connection with shear device 40 (at inlet 205 in FIG. 1), wherein said fluid connection may be any as known to one skilled in the art. The temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid connection (at outlet 210 in FIG. 1) with vessel 50, wherein said fluid connection may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow into vessel 50. Pump 45 is configured for either continuous or semi-continuous operation, and may be any suitable pumping device. Processed therapeutic fluids 55 are then administered to patients via a catheter intravenously. The methods of administering processed therapeutic fluids 55 to patients may be any known to one skilled in the art, such as intravenous injection and/or intravenous infusion.

Destruction of Cancer Cells

In some embodiments, the application of shear stress is especially useful in ex-situ direct treatment of blood from patients affected by hematological malignancies, such as leukemia, lymphoma, multiple myeloma. Because cancer cells are more vulnerable to shear stress than healthy/normal cells, shear stress with a well-configured shear device is applied in a way that predominantly destroys cancerous cells either acutely or chronically without significantly jeopardizing the health or function of normal cells. Destroying the cancer cells acutely means that the cancer cells are killed during the application of shear. Destroying the cancer cells chronically means that the cancer cells are killed not in instantly but gradually, for example after the cancer cells are returned to the patient's body via infusion.

Selection of the shear device, shear rate, shear stress, and residence time applied in shear device 200 depends on the vitality of healthy cells, the vulnerability of cancer cells, and the amount of blood to be processed from the patients. The operational parameters are adjusted so that mainly cancer cells are destroyed by being directly subjected ex-situ to a certain level of shear stress for a period of time, wherein healthy cells are not significantly affected under said conditions. When the processed blood is re-circulated into patients intravenously, cancer cell debris is cleared from the bloodstream by normal liver function.

Figure 3A:
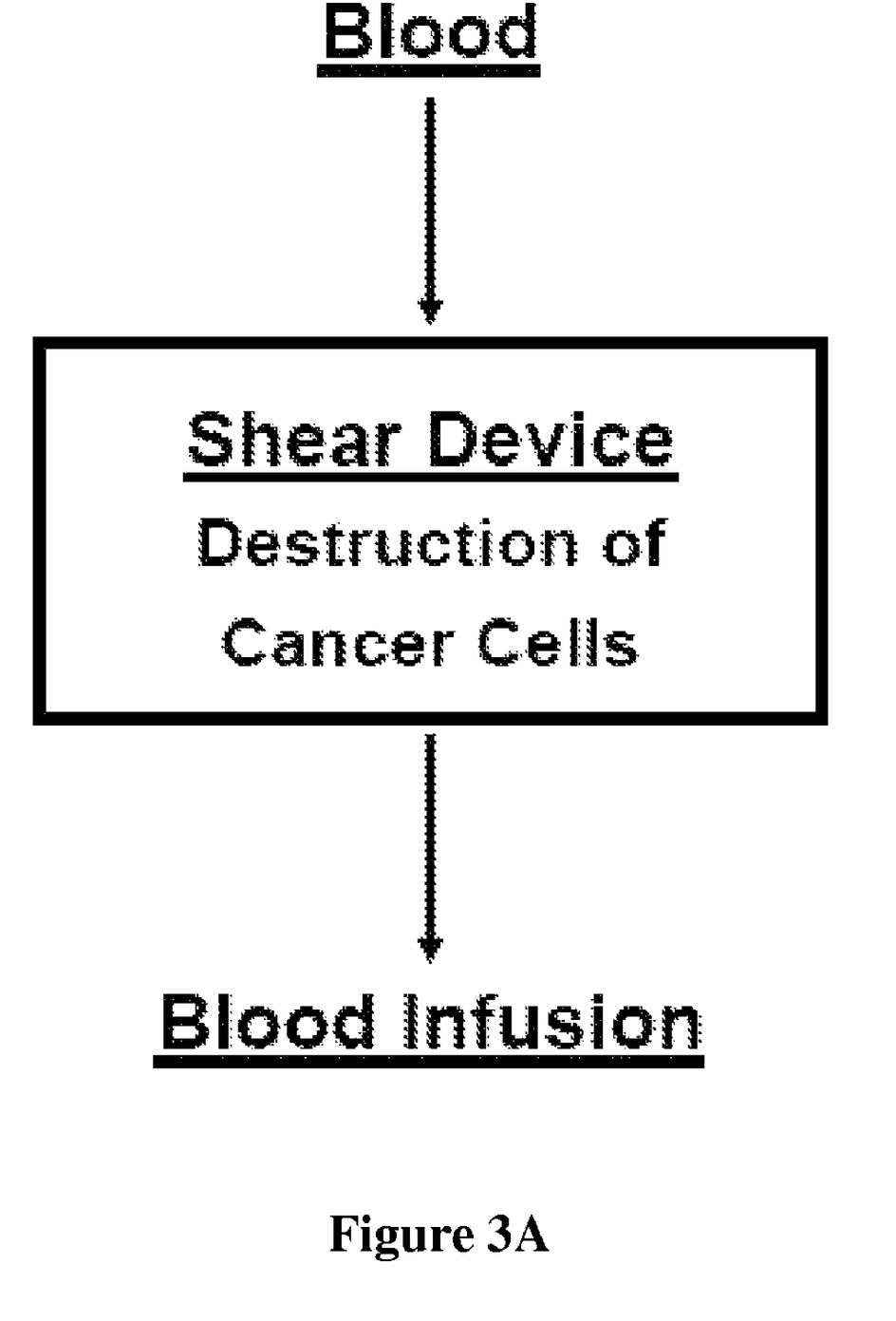
FIG. 3A illustrates a method of utilizing the shear device ex-situ for destruction of cancer cells.
Figure 3B:
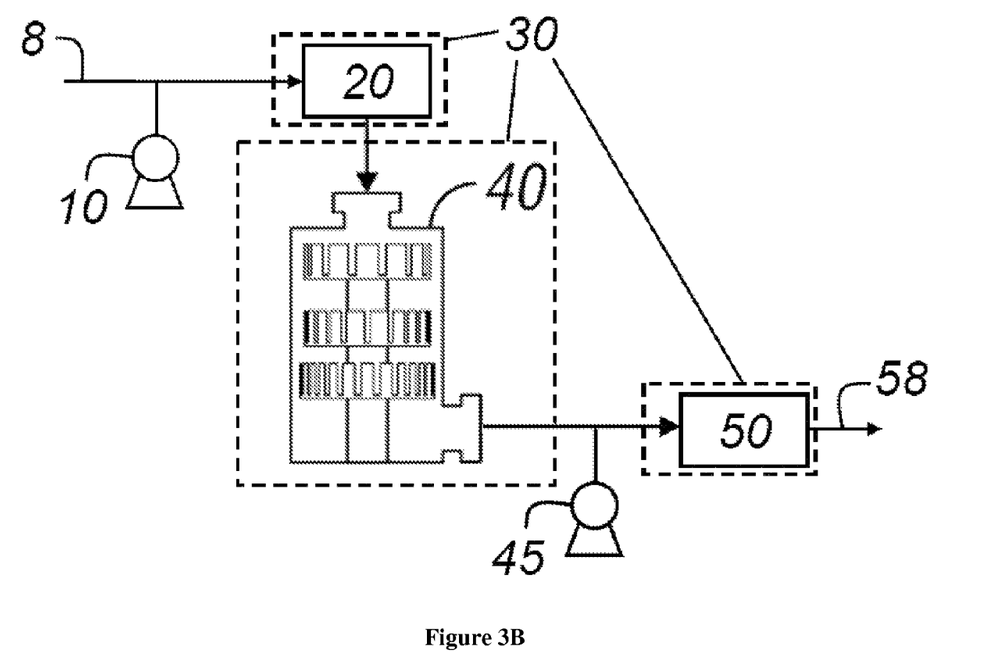
FIG. 3B is a process flow diagram demonstrating the application of shear stress ex-situ for destruction of cancer cells.

In exemplary embodiments (FIG. 3A and FIG. 3B), blood 8 from patients is extracted, transported, and stored in a vessel 20 with a temperature control unit 30. The extraction of blood from patients is achieved by any method known to one skilled in the art. The temperature control unit 30 is any device known to one skilled in the art and has the capacity to maintain a temperature between 0-100° C. within ±2° C. fluctuations. In some embodiments a combination of shear and temperature is used to accomplish the desired effect of destroying predominantly cancer cells. In some embodiments, a pump 10 is included to control the flow into vessel 20. Pump 10 is configured for either continuous or semi-continuous operation, and may be any suitable pumping device. Vessel 20 is configured to be in fluid connection with shear device 40 (at inlet 205 in FIG. 1), wherein said fluid connection may be any as known to one skilled in the art. The temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid connection (at outlet 210 in FIG. 1) with vessel 50, wherein said fluid connection may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow into vessel 50. Pump 45 is configured for either continuous or semi-continuous operation, and may be any suitable pumping device. Processed blood 58 is then re-circulated into patients via a catheter intravenously. The methods of administering processed blood 58 to patients may be any known to one skilled in the art, such as intravenous infusion.

Drug Delivery and Destruction of Cancer Cells

In some embodiments, shear stress is applied to the mixture of therapeutic fluids and blood from patients. Potential effects include (1) acute or chronic cancer cell death, but not healthy cells, by being directly subjected to shear stress; (2) dispersion of drugs into nano-size or sub-nano-size particles to increase drug delivery efficiency and drug efficacy; (3) intra-cellular uptake of drugs into cancer cells, resulting in acute or chronic cancer cell death; (4) drug loading into healthy cells without jeopardizing their health or function; (5) constitution of cell therapy by delivering drugs to targeted site of drug action by incorporating drugs into cells and releasing drugs from cells to said targeted site of drug action through blood circulation. Both normal cells and cancer cells may be used for the constitution of cell therapy. The therapeutic agent that was taken into the normal cells or cancer cells or both is released at the targeted site to treat the on-site cancer cells. In some cases, the application of shear activates chemotherapy drugs by creating free radicals. These free radicals are capable of destroying cancer cells, causing acute or chronic cancer cell death. Thus the application of shear increases the efficacy of the chemotherapy drugs.

Selection of the shear device, shear rate, shear stress, and residence time applied in shear device 200 depends on (1) vitality of the healthy cells; (2) vulnerability of the cancer cells; (3) amount of therapeutic fluid/dispersion administered; (4) amount of blood to be processed; (5) nature of the components of the therapeutic fluids utilized; (6) desired extent of drug loading into cells. The operational parameters are adjusted so that mainly cancer cells are destroyed by being directly subjected ex-situ to a certain level of shear stress for a period of time, wherein healthy cells are not significantly affected under said conditions. The operational parameters are further adjusted according to the objectives of tasks at hand, which dictate the specific requirements for the therapeutic fluids. For example, the application of shear stress continues for a period of time at a particular shear stress level so that a desired amount of drugs is loaded into cancer cells to cause cancer cell death with minimum loading of drugs into normal cells so as to maintain the health of these cells with normal function. When the processed mixture of blood and therapeutic fluids is re-circulated into patients intravenously, cancer cell debris is cleared from the bloodstream by normal liver function; drugs and drug-loaded cells travel in the bloodstream, resulting in drug action at target sites for disease treatment.

Figure 4A:
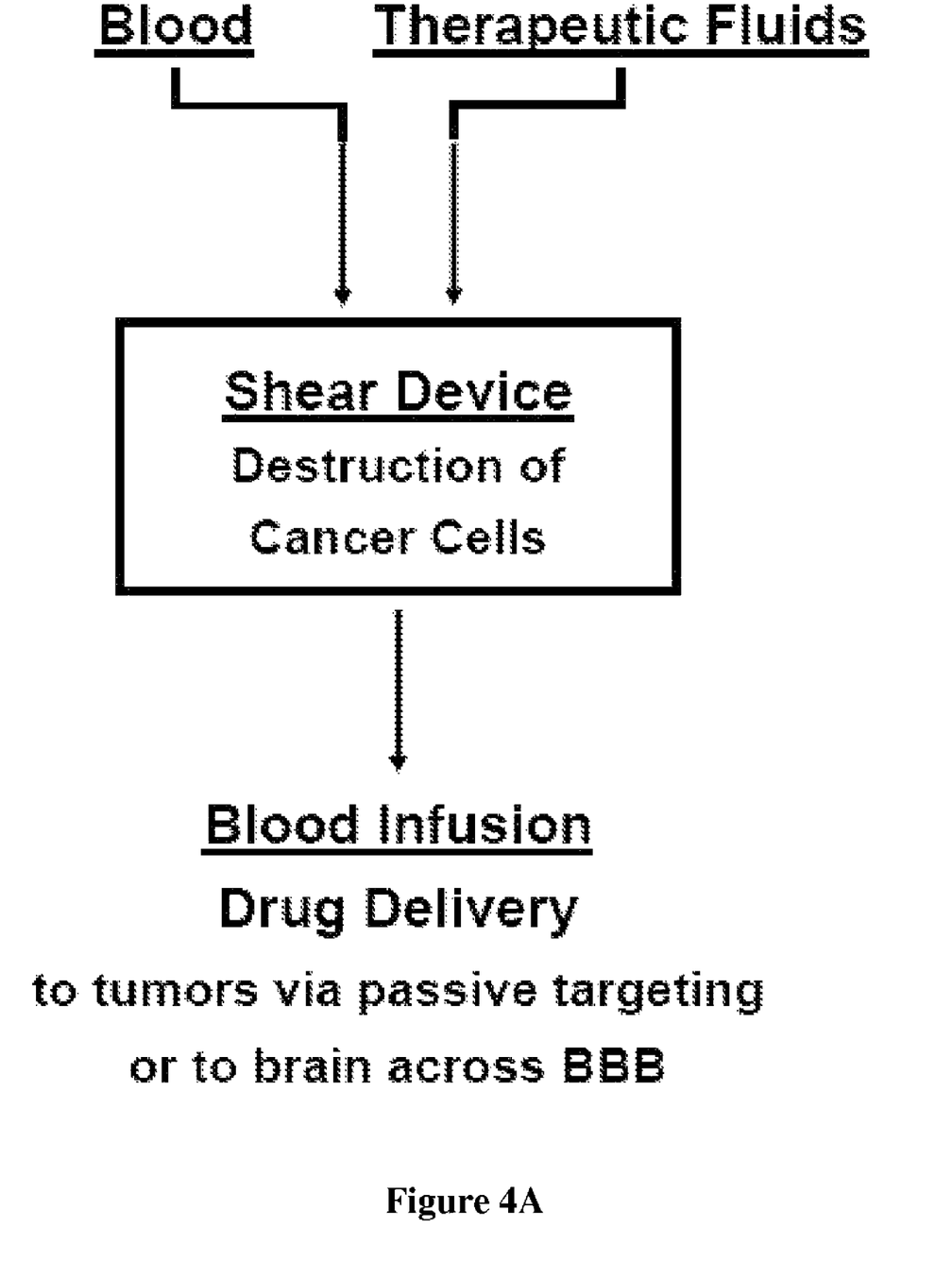
FIG. 4A illustrates a method of utilizing the shear device ex-situ for drug delivery and destruction of cancer cells.

In exemplary embodiments (FIG. 4A), after blood is extracted from patients, therapeutic fluids are added into the blood, and the mixture is passed shear device (200 in FIG. 1). The processed mixture is then re-circulated into the patients by any method known to one skilled in the art (e.g., blood infusion). In the shear device, direct application of shear stress causes cancer cell death without jeopardizing the health of the normal cells. At the same time, drugs are dispersed into the mixture in either an intra-cellular form or an extra-cellular form so that when the mixture is re-circulated into the patients, drugs are delivered to the desired site of action via blood circulation, including brain tissue and cancerous tissue, with increased drug efficacy.

In exemplary embodiments (FIG. 4B), blood 8 from patients is extracted and mixed with therapeutic fluids 5 in vessel 9 with a temperature control unit 30. The extraction of blood from patients is achieved by any method known to one skilled in the art. The temperature control unit 30 is any device known to one skilled in the art and has the capacity to maintain a temperature between 0-100° C. within ±2° C. fluctuations. In alternative embodiments, mixing vessel 9 is omitted. Mixing vessel 9 is configured to be in fluid connection with vessel 20. In exemplary embodiments, the temperature of vessel 20 is maintained by a temperature control unit 30. The temperature control unit 30 is any device known to one skilled in the art and has the capacity to maintain a temperature between 0-100° C. within ±2° C. fluctuations. In some embodiments a combination of shear and temperature is used to accomplish the desired effect of destroying predominantly cancer cells.

Figure 4B:
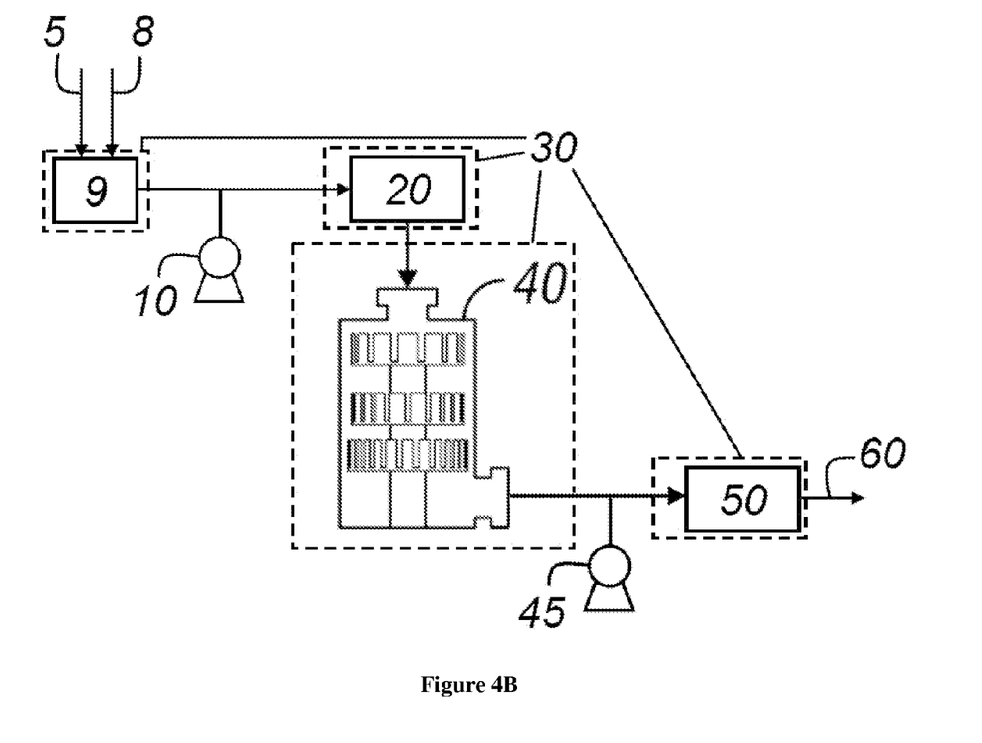
FIG. 4B is a process flow diagram demonstrating the application of shear stress ex-situ for drug delivery and destruction of cancer cells.

In some embodiments, a pump 10 is included to control the flow into vessel 20. Pump 10 is configured for either continuous or semi-continuous operation, and may be any suitable pumping device. Vessel 20 is configured to be in fluid connection with shear device 40 (at inlet 205 in FIG. 1), wherein said fluid connection may be any as known to one skilled in the art. The temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid connection (at outlet 210 in FIG. 1) with vessel 50, wherein said fluid connection may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow into vessel 50. Pump 45 is configured for either continuous or semi-continuous operation, and may be any suitable pumping device. Processed blood-therapeutics mixture 60 is then re-circulated into patients via a catheter intravenously. The methods of administering processed mixture 60 to patients may be any known to one skilled in the art, such as intravenous infusion.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of preparing a fluid for intravenous administration to a patient; comprising:
    obtaining a system for applying shear stress ex-situ to a fluid, the system comprising a shear device; and at least one device configured for intravenous administration of said fluid to a patient, said devices defining a fluid passage configured to be sterilized and maintained sterile during use, said fluid comprising a therapeutic fluid comprising a therapeutic agent or blood and a therapeutic fluid comprising a therapeutic agent, wherein said fluid passage is sterile;
    applying shear stress to said fluid; and
    maintaining sterility of said fluid and fluid passage;
    wherein shear stress is applied to the fluid to disperse the therapeutic agent contained therein to its nano-size or sub-nano-size form.

2. The method of claim 1 wherein the fluid comprises the patient's blood containing both cancer cells and normal blood cells, and applying said shear stress to the fluid destroys mainly cancer cells acutely or chronically without significantly affecting the health or function of the normal cells.

3. The method of claim 1 wherein the fluid comprises a mixture of the patient's blood containing both cancer cells and normal blood cells, and at least one therapeutic agent, and applying the shear stress to the fluid causes at least one of the following effects:
    a. destroying mainly cancer cells acutely or chronically without significantly affecting the health or function of the normal cells;
    b. dispersing the at least one therapeutic agent to a nano-size or sub-nano-size form;
    c. causing intracellular uptake of at least one said therapeutic agent by the cancer cells, resulting in acute or chronic cancer cell death;
    d. causing intracellular uptake of at least one said therapeutic agent by the normal cells without significantly affecting their health or function.

4. The method of claim 1 wherein the fluid comprises at least one therapeutic agent, and applying the shear stress to said fluid activates the at least one said therapeutic agent.

5. The method of claim 4 wherein activating the at least one therapeutic agent comprises creating free radicals of the at least one therapeutic agent.

6. The method of claim 1 further comprising controlling temperature of said fluid, wherein shear stress is applied simultaneously with the control of temperature.

7. The method of claim 1 further comprising controlling the shear stress applied to fluid passing through the shear device.

8. The method of claim 1 further comprising controlling the residence time of fluid passing through the shear device.

9. The method of claim 1 further comprising controlling the flow rate of fluid through the shear device.

10. The method of claim 1 wherein the fluid comprises at least one therapeutic agent in the form of a solid, liquid, gas, solution, gel, emulsion, powder or a combination of any of those forms.

11. A method of performing cell therapy in a patient, comprising:

performing the method of claim 1, wherein the fluid comprises a therapeutic agent and normal blood cells or cancer cells or both, and wherein applying shear stress to the fluid causes intracellular uptake of at least one said therapeutic agent by the normal blood cells or cancer cells or both without significantly affecting the health or function of the normal blood cells;

administering the fluid to the patient intravenously to deliver the cells containing the at least one therapeutic agent to a targeted site of agent action in the patient's body through blood circulation; and causing the cells containing the at least one therapeutic agent to release the at least one agent at the targeted site.

* * * * *